United States Patent
Broekhuis et al.

(10) Patent No.: US 12,415,791 B2
(45) Date of Patent: *Sep. 16, 2025

(54) PROCESS FOR PRODUCING ETHYLENE OXIDE FROM ETHANE BY OXIDATIVE DEHYDROGENATION AND EPOXIDATION WITH SPLIT RECYCLE

(71) Applicants: SABIC Global Technologies, B.V., Bergen Op Zoom (NL); Robert Roger Broekhuis, Sugar Land, TX (US); Pankaj Singh Gautam, Sugar Land, TX (US); Tian Gu, Sugar Land, TX (US); Vidya Sagar Reddy Sarsani, Sugar Land, TX (US)

(72) Inventors: Robert Roger Broekhuis, Sugar Land, TX (US); Pankaj Singh Gautam, Sugar Land, TX (US); Tian Gu, Sugar Land, TX (US); Vidya Sagar Reddy Sarsani, Sugar Land, TX (US)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 550 days.

This patent is subject to a terminal disclaimer.

(21) Appl. No.: 17/908,476

(22) PCT Filed: Mar. 5, 2021

(86) PCT No.: PCT/US2021/021174
§ 371 (c)(1),
(2) Date: Aug. 31, 2022

(87) PCT Pub. No.: WO2021/183390
PCT Pub. Date: Sep. 16, 2021

(65) Prior Publication Data
US 2023/0242497 A1    Aug. 3, 2023

Related U.S. Application Data

(60) Provisional application No. 62/987,176, filed on Mar. 9, 2020.

(51) Int. Cl.
*C07D 301/08* (2006.01)

(52) U.S. Cl.
CPC .................. *C07D 301/08* (2013.01)

(58) Field of Classification Search
CPC ........................ C07D 301/08; C07D 303/04
(Continued)

(56) References Cited

U.S. PATENT DOCUMENTS

| 5,008,414 A | 4/1991 | Ramachandran et al. |
| 5,817,841 A | 10/1998 | Baker et al. |

(Continued)

FOREIGN PATENT DOCUMENTS

| CN | 103328457 A | 9/2013 |
| CN | 103391929 A | 11/2013 |

(Continued)

OTHER PUBLICATIONS

Foreign communication from related application—International Search Report and Written Opinion dated Jun. 28, 2021 for application No. PCT/US2021/021174 filed Mar. 5, 2021, 9 pages.

(Continued)

*Primary Examiner* — Taylor V Oh
(74) *Attorney, Agent, or Firm* — Conley Rose, P.C.; Rodney B. Carroll

(57) ABSTRACT

An ethylene oxide (EO) production process comprising (a) introducing a first reactant mixture ($C_2H_6$, $O_2$) to a first reactor to produce a first effluent stream ($C_2H_4$, $C_2H_6$, $O_2$); (b) introducing a second reactant mixture to a second reactor to produce a second effluent stream (EO, $C_2H_4$, $C_2H_6$, $O_2$); wherein the second reactant mixture comprises at least a portion of first effluent stream; (c) separating the second effluent stream into an EO product stream (EO) and recycle stream ($C_2H_4$, $C_2H_6$, $O_2$); wherein ethylene is not separated from recycle stream and/or first effluent stream; and (d)

(Continued)

recycling a first portion of recycle stream to the first reactor, and a second portion of recycle stream to the second reactor; wherein recycle split ratio <0.6; and wherein recycle split ratio is defined as ratio of volumetric flowrate of first portion of recycle stream divided by the sum of volumetric flowrates of first portion and second portion of recycle stream.

20 Claims, 1 Drawing Sheet

(58) Field of Classification Search
USPC .......................................................... 549/523
See application file for complete search history.

(56) References Cited

U.S. PATENT DOCUMENTS

| | | |
|---|---|---|
| 6,040,467 A | 3/2000 | Papavassiliou et al. |
| 8,105,971 B2 | 1/2012 | Gaffney et al. |
| 8,148,555 B2 | 4/2012 | Lockemeyer et al. |
| 8,519,210 B2 | 8/2013 | Arnold et al. |
| 8,846,996 B2 | 9/2014 | Kustov et al. |
| 8,969,602 B2 | 3/2015 | Verhaak |
| 9,139,544 B2 | 9/2015 | Jovanovic et al. |
| 9,545,610 B2 | 1/2017 | Simanzhenkov et al. |
| 9,649,621 B2 | 5/2017 | Shibata et al. |
| 2014/0018557 A1 | 1/2014 | Verhaak |
| 2015/0251979 A1 | 9/2015 | Verhaak et al. |

FOREIGN PATENT DOCUMENTS

| | | |
|---|---|---|
| CN | 108025998 A | 5/2018 |
| CN | 108947938 A | 12/2018 |
| EP | 0893443 A2 | 1/1999 |
| WO | 2002085875 A1 | 10/2002 |
| WO | 2013144064 A1 | 10/2013 |
| WO | 2019197249 A1 | 10/2019 |
| WO | 2004078736 A1 | 9/2024 |

OTHER PUBLICATIONS

Foreign communication from related application—International Preliminary Report on Patentability dated Sep. 6, 2022 for application No. PCT/US2021/021174 filed Mar. 5, 2021, 7 pages.

SA office action issued on Apr. 30, 2025 for the patent Application No. 522440457 dated Sep. 8, 2022, 7 pages.

PROCESS FOR PRODUCING ETHYLENE OXIDE FROM ETHANE BY OXIDATIVE DEHYDROGENATION AND EPOXIDATION WITH SPLIT RECYCLE

CROSS REFERENCE TO RELATED APPLICATION

This application is a filing under 35 U.S.C. 371 of International Application No. PCT/US2021/021174 filed Mar. 5, 2021, entitled "Process for Producing Ethylene Oxide from Ethane by Oxidative Dehydrogenation and Epoxidation with Split Recycle," which claims priority to U.S. Provisional Application No. 62/987,176 filed Mar. 9, 2020, which applications are incorporated by reference herein in their entirety.

TECHNICAL FIELD

The present disclosure relates to a process for the production of ethylene oxide, more specifically a process for the production of ethylene oxide that integrates oxidative dehydrogenation of ethane with ethylene epoxidation.

BACKGROUND

Ethylene oxide (EO) is an important petrochemical intermediate, and it is a starting material for the production of ethylene glycol, as well as other glycols (e.g., polyethylene glycols), ethoxylates, ethanol-amines, solvents, and glycol ethers. EO is currently produced using a sequence of conventional ethylene production technology (e.g., steam cracking, such as ethane steam cracking) and conventional ethylene oxide production technology (e.g., catalytic epoxidation). Steam cracking is a capital-intensive process with incomplete selectivity to ethylene.

Ethane oxidative dehydrogenation (ODH) technology has been contemplated for the production of ethylene with subsequently using the produced ethylene to yield EO, but such a process has not yet found significant commercial application. Subsequent to the recovery of the EO, the stream containing unconverted ethylene and ethane could be separated into an ethane-rich stream that could be recycled to the ODH reactor and an ethylene-rich stream that can be recycled to the EO reactor, but such separation is very costly, owing in part to the large stream volume that would need to undergo the separation. Further, such a separation would be conventionally carried out by cryogenic distillation; and undertaking a large-scale cryogenic separation of the stream containing unconverted ethylene and ethane obtained after the recovery of EO, given associated refrigeration loads and distillation tower sizes, would be prohibitively expensive. Thus, there is an ongoing need for the development of processes that combine the ODH and EO technologies, while providing for an increased chemical efficiency and/or lower capital cost.

BRIEF DESCRIPTION OF THE DRAWINGS

For a detailed description of the preferred embodiments of the disclosed methods, reference will now be made to the accompanying drawing in which.

DETAILED DESCRIPTION

Figure 1:
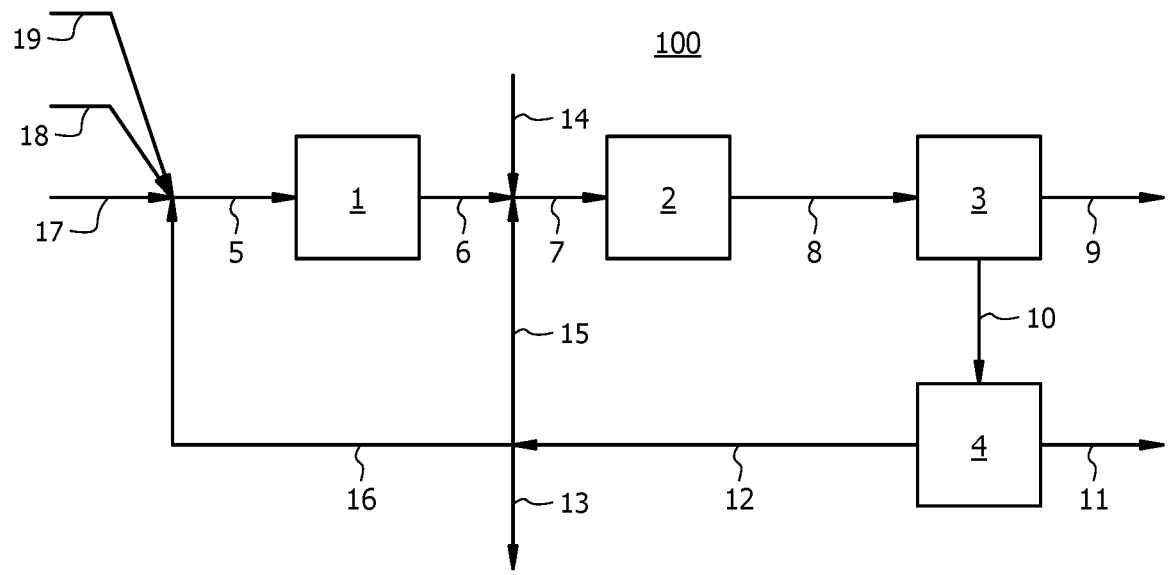
FIG. 1 displays a schematic of a system for an ethylene oxide (EO) production process.

Disclosed herein are processes for producing ethylene oxide (EO) comprising using (i) a first catalytic reactor (e.g., oxidative dehydrogenation (ODH) reactor) for converting ethane to ethylene by ODH and (ii) a second catalytic reactor (e.g., EO reactor) for converting ethylene to EO. The processes for producing EO as disclosed herein can advantageously provide for higher overall carbon efficiency and/or lower overall capital intensity than conventional processes for the production of EO, for example a conventional process employing an ethane steam cracker combined with an EO reactor. The processes for producing EO as disclosed herein can advantageously provide for configurations of systems for EO production that enhance capital efficiency and/or carbon efficiency of an integrated process (i.e., a process that integrates ODH and EO technologies) that converts an ethane feedstock to EO, wherein the produced EO can be subsequently converted to ethylene glycol. The ODH and EO reactors as disclosed herein can be advantageously operated in a recycle configuration, wherein substantially all of the effluent from the ODH reactor can be directed to the EO reactor, and wherein the unreacted part of the effluent from the EO reactor (i.e., after EO recovery) can be recycled partly to the ODH reactor and partly to the EO reactor. In this recycle process (i.e., the process for producing EO as disclosed herein), there is no need to separate of ethylene from ethane in the unreacted part of the effluent from the EO reactor. Further, there is substantially no need to separate unconverted oxygen in the process, since oxygen is conveniently and advantageously recycled back to the ODH and EO reactors.

The processes for producing EO as disclosed herein advantageously recycle a significant portion (e.g., greater than about 40%) of the recycle flow (i.e., unreacted part of the effluent from the EO reactor) to the EO reactor, wherein a smaller portion of the recycle flow is returned to the ODH reactor. The processes for producing EO as disclosed herein can advantageously introduce oxygen make-up streams to each of the ODH reactor and the EO reactor. Further, the processes for producing EO as disclosed herein can advantageously control process performance by varying the recycle split ratio (i.e., the split ratio of the recycle flow between the ODH and the EO reactors).

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

For purposes of the disclosure herein, the term "reactor" is understood to encompass one or more reaction zones; one or more reaction stages; one or more reaction vessels; or combinations thereof.

Unless defined otherwise, technical and scientific terms used herein have the same meaning as is commonly understood by one of skill in the art.

Referring to the configuration of FIG. 1, an ethylene oxide (EO) production system 100 is disclosed. EO production system 100 generally comprises a first reactor or an oxidative dehydrogenation (ODH) reactor 1; a second reactor or an EO reactor 2; a product recovery system 3; and a carbon dioxide ($CO_2$) removal system 4.

Figure 2:
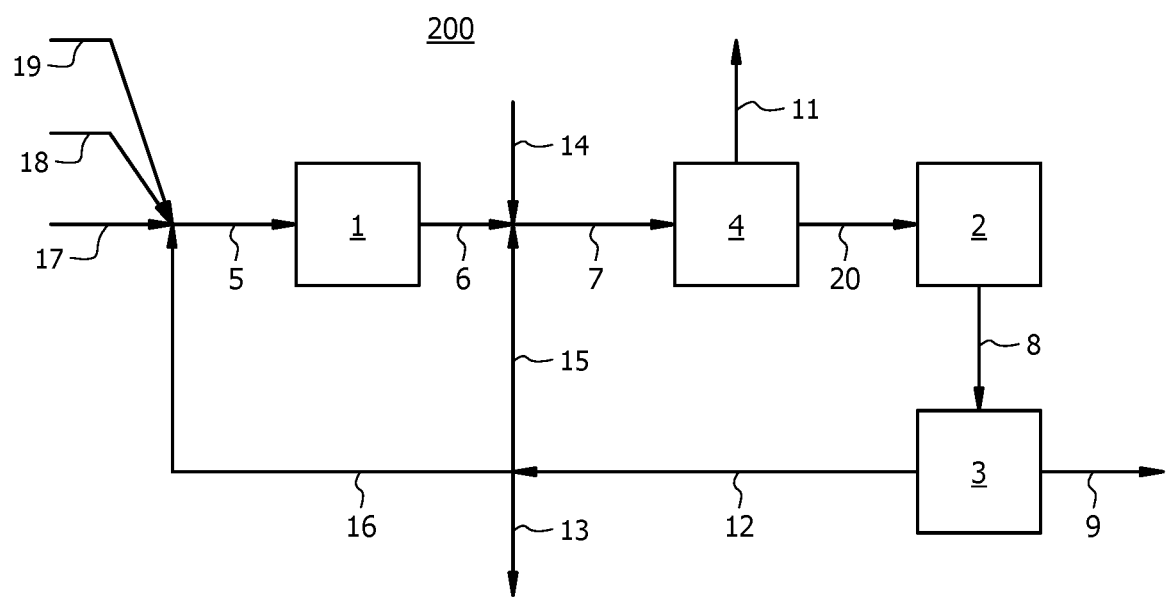
FIG. 2 displays another schematic of a system for an EO production process.

Referring to the configuration of FIG. 2, an ethylene oxide (EO) production system 200 is disclosed. EO production system 200 generally comprises a first reactor or an ODH reactor 1; a second reactor or an EO reactor 2; a product recovery system 3; and a $CO_2$ removal system 4. As will be appreciated by one of skill in the art, and with the help of this disclosure, EO production system components shown in FIGS. 1-2 can be in fluid communication with each other (as represented by the connecting lines indicating a direction of fluid flow) through any suitable conduits (e.g., pipes, streams, etc.). Further, and as will be appreciated by one of skill in the art, and with the help of this disclosure, EO production systems 100 and 200 depicted in FIGS. 1-2 may further comprise additional operations and/or equipment, such as compressors, heaters, coolers, water removal systems, etc. Common reference numerals refer to common components present in one or more of the Figures, and the description of a particular component is generally applicable across respective Figures wherein the component is present, except as otherwise indicated herein.

In an aspect, a process for producing EO as disclosed herein can comprise a step of introducing a first reactant mixture (e.g., ODH reactor feed stream 5) to the ODH reactor 1 to produce a first effluent stream (e.g., ODH reactor effluent stream 6); wherein the first reactant mixture comprises ethane ($C_2H_6$), and oxygen ($O_2$); and wherein the first effluent stream comprises ethylene ($C_2H_4$), ethane, and oxygen. The first reactant mixture further comprises ethylene, wherein the mole fraction of ethylene in the first effluent stream is greater than the mole fraction of ethylene in the first reactant mixture. In some aspects, ethane, ethylene and oxygen may be fed to the ODH reactor 1 together, for example via ODH reactor feed stream 5, as displayed in the configuration of FIGS. 1 and 2. In other aspects, ethane, ethylene and oxygen may be fed to the ODH reactor 1 separately, wherein one or more components of the first reactant mixture may be fed to the ODH reactor 1 separately. For example, a stream comprising ethylene and ethane and a separate stream comprising oxygen may be fed to the ODH reactor 1 separately (e.g., without contacting each other prior to introducing to the ODH reactor 1).

In some aspects, for example as displayed in the configuration of FIGS. 1-2, a recycle stream (e.g., ODH recycle feed stream 16) recovered from the EO production process may be combined with one or more streams to produce the ODH reactor feed stream 5. For example, ODH recycle feed stream 16 may be combined with an ethane feed stream 17, an ODH oxygen make-up feed stream 18, and optionally with a ballast gas make-up stream 19 to yield the ODH reactor feed stream 5. ODH recycle feed stream 16 comprises ethylene, ethane, oxygen, and a ballast gas, and it will be described in more detail later herein. Ethane feed stream 17 provides for supplemental ethane or "fresh" ethane, which replenishes the ethane that has been consumed (e.g., via ODH reaction in reactor 1, undesired side reactions in EO reactor 2) and/or lost (e.g., via purge stream 13) in the process. For purposes of the disclosure herein, the term "fresh" component (e.g., fresh ethane, fresh oxygen, fresh methane, etc.) refers to a component of a reactant mixture (e.g., first reactant mixture, second reactant mixture, etc.) that does not comprise the component recovered from the process and recycled back into the process, but rather refers to a supplemental source of such component which is introduced to the reactant mixture.

In some aspects, the first reactant mixture can be characterized by a molar ratio of ethylene to ethane of equal to or greater than about 1.3, equal to or greater than about 1.5, equal to or greater than about 2.0, equal to or greater than about 2.1, equal to or greater than about 2.2, equal to or greater than about 2.3, equal to or greater than about 2.4, or equal to or greater than about 2.5, from about 1.3 to about 3.0, from about 1.5 to about 2.7, or from about 2.0 to about 2.6. In other aspects, the first reactant mixture can be characterized by a molar ratio of ethylene to ethane of less than about 1.3, less than about 1.0, or less than about 0.5, from about 0.1 to less than about 1.3, from about 0.2 to about 1.0, or from about 0.3 to about 0.8.

In an aspect, the ODH oxygen make-up feed stream 18 can be provided to the ODH reactor 1. Stream 18 can be oxygen gas, technical oxygen (which can contain some air), air, oxygen enriched air, and the like, or combinations thereof. In an aspect, stream 18 comprises substantially pure oxygen (e.g., oxygen having less than about 1 vol. % contaminants, such as nitrogen ($N_2$), argon (Ar), etc.). The ODH oxygen make-up feed stream 18 provides for supplemental oxygen or fresh oxygen, which replenishes the oxygen that has been consumed (e.g., via ODH reaction in reactor 1, EO reaction in EO reactor 2, combustion reactions in reactors 1 and 2, etc.) and/or lost (e.g., via purge stream 13) in the process.

In an aspect, the ballast gas make-up stream 19 can be provided to the ODH reactor 1. Generally the term "ballast gas" refers to a diluent gas (e.g., gaseous compound or combination of gaseous compounds) that is introduced to a particular reactor, wherein the diluent gas does not significantly participate in chemical reactions in that particular reactor. Ballast gases can be used for the purposes of diluting reacting components in a reactor feed, providing better chemical and/or thermal control of a reactor, etc.

Nonlimiting examples of ballast gases suitable for use in the present disclosure include methane ($CH_4$), $N_2$, steam, noble gases, such as Ar, and the like, or combinations thereof. In an aspect, the ballast gas make-up stream 19 comprises methane.

The ODH reactor 1 can be any suitable reactor, such as a continuous flow reactor, a fixed bed reactor, a fluidized bed reactor, and the like, or combinations thereof. In an aspect, the ODH reactor 1 comprises a continuous flow fixed bed reactor.

In an aspect, the ODH reactor 1 can be characterized by an ODH reactor operating temperature of from about 240° C. to about 400° C., from about 250° C. to about 375° C., from about 260° C. to about 350° C., or from about 270° C. to about 340° C. The ODH reactor operating temperature is defined as the average of ODH reactor inlet temperature and ODH reactor outlet temperature. For purposes of the disclosure herein, the term "inlet temperature" (e.g., reactor inlet temperature) refers to the temperature of the feed gas (e.g., first reactant mixture; second reactant mixture) at the point it first comes into contact with the catalyst (e.g., ODH catalyst; EO catalyst), which inlet temperature may be higher than the temperature of fresh feed introduced into the reactor, for example because the feed has been preheated within the reactor. Further, for purposes of the disclosure herein, the term "outlet temperature" (e.g., reactor outlet temperature) refers to the temperature of the effluent at the outlet out of the reactor.

In an aspect, the ODH reactor 1 can be characterized by an ODH reactor operating pressure of from about 1 barg to about 35 barg, from about 3 barg to about 30 barg, from about 5 barg to about 25 barg, or from about 10 barg to about 20 barg. The ODH reactor operating pressure can be substantially the same as an EO reactor operating pressure. In some aspects, the ODH reactor operating pressure can be from about 1 barg to about 10 barg greater than the EO reactor operating pressure, thereby avoiding the need for excessive compression.

In an aspect, the ODH reactor 1 comprises an ODH catalyst. The ODH catalyst comprises any ODH catalyst suitable for catalyzing an ODH reaction. For example, the ODH catalyst can comprise a mixed metal oxide, such as a mixed metal oxide comprising molybdenum, vanadium, niobium, tellurium, and the like, or combinations thereof. The ODH reactor, ODH catalyst, and ODH operating conditions (e.g., pressure, temperature) are described in more detail in U.S. Pat. Nos. 8,105,971; 8,519,210; 8,846,996; and 9,545,610; each of which is incorporated by reference herein in its entirety.

The ethane introduced to the ODH reactor 1 contacts the ODH catalyst and, in the presence of oxygen, is converted to ethylene via the ODH reaction (1):

$$C_2H_6 + \tfrac{1}{2}O_2 \rightarrow C_2H_4 + H_2O \tag{1}$$

Several side reactions or unwanted reactions (i.e., reactions other than ethane conversion to ethylene via the ODH reaction) can take place in the ODH reactor 1, as follows. A portion of the ethylene, as well as a portion of the ethane in the ODH reactor 1 can be converted to oxygenated organic compounds, such as aldehydes and/or carboxylic acids; acetylene; carbon dioxide ($CO_2$); optionally carbon monoxide (CO); water; and the like; or combinations thereof.

In an aspect, the ODH reactor 1 can be characterized by an oxygen conversion of equal to or greater than about 30%, equal to or greater than about 45%, or equal to or greater than about 60%, from about 30% to about 100%, from about 45% to about 100%, from about 45% to about 99%, or from about 60% to about 97.5%.

In an aspect, the ODH reactor 1 can be characterized by an ethane conversion of equal to or greater than about 60%, equal to or greater than about 65%, equal to or greater than about 70%, equal to or greater than about 75%, equal to or greater than about 80%, equal to or greater than about 85%, or equal to or greater than about 90%; from about 60% to about 100%, from about 65% to about 99.9%, from about 70% to about 99.5%, from about 75% to about 99%, from about 80% to about 98.5%, from about 85% to about 98%, or from about 90% to about 97.5%.

In an aspect, the ODH reactor 1 can be characterized by an ethane conversion of equal to or greater than about 70%. For example, the ODH reactor 1 can be characterized by an ethane conversion of equal to or greater than about 70%, equal to or greater than about 75%, equal to or greater than about 80%, equal to or greater than about 85%, or equal to or greater than about 90%; from about 70% to about 100%, from about 75% to about 99%, from about 80% to about 98.5%, from about 85% to about 98%, or from about 90% to about 97.5%.

The ODH reactor effluent stream 6 can be recovered from the ODH reactor 1, wherein the ODH reactor effluent stream 6 can comprise ethylene, ethane, oxygen, carbon dioxide, and water. The ODH reactor effluent stream 6 can further comprise the ballast gas (e.g., methane), and optionally acetic acid, acetylene, CO, or combinations thereof. In an aspect, ethylene is not separated from the ODH reactor effluent stream 6; i.e., ethylene is not separated from the ethane in the ODH reactor effluent stream 6, prior to introducing the ethylene in the ODH reactor effluent stream 6 into the EO reactor 2.

In an aspect, the ODH reactor effluent stream 6 can be characterized by an ethane concentration of less than about 30 mol %, less than about 25 mol %, less than about 20 mol %, less than about 15 mol %, less than about 10 mol %, less than about 7.5 mol %, less than about 5 mol %, less than about 4 mol %, less than about 3 mol %, less than about 2 mol %, or less than about 1 mol %; from about 0.01 mol % to about 30 mol %, from about 0.02 mol % to about 25 mol %, from about 0.03 mol % to about 20 mol %, from about 0.04 mol % to about 15 mol %, from about 0.05 mol % to about 10 mol %, from about 0.07 mol % to about 7.5 mol %, or from about 0.1 mol % to about 5 mol %.

In an aspect, the ODH reactor effluent stream 6 can be characterized by an ethane concentration of less than about 5 mol %, or from about 0.1 mol % to about 5 mol %. For example, the ODH reactor effluent stream 6 can be characterized by an ethane concentration of less than about 5 mol %, less than about 4 mol %, less than about 3 mol %, less than about 2 mol %, or less than about 1 mol %; from about 0.1 mol % to about 5 mol %, from about 0.15 mol % to about 4 mol %, from about 0.2 mol % to about 3 mol %, from about 0.25 mol % to about 2 mol %, or from about 0.3 mol % to about 1 mol %.

Although ethane is not separated from the ethylene in the ODH reactor effluent stream 6, at least a portion of components other than ethylene, ethane, and oxygen may be separated from (e.g., removed from) ODH reactor effluent stream 6, prior to introducing the ethylene, ethane, and oxygen in the ODH reactor effluent stream 6 into the EO reactor 2.

In an aspect, at least a portion of the water and at least a portion of the acetic acid (if acetic acid is formed in the ODH reactor 1) can be removed from the ODH reactor effluent stream 6, for example by condensation (e.g., lowering the stream temperature to promote condensation), to yield a dehydrated ODH reactor effluent stream.

In an aspect, at least a portion of the carbon dioxide can be removed from the ODH reactor effluent stream 6 and/or dehydrated ODH reactor effluent stream to yield a $CO_2$-depleted ODH reactor effluent stream 20, for example as displayed in the configuration of FIG. 2.

Referring to the configuration of FIG. 2, the ODH reactor effluent stream 6 and/or dehydrated ODH reactor effluent stream can be combined with one or more streams (e.g., a recycle stream, such as EO recycle feed stream 15; an EO oxygen make-up feed stream 14; optionally with a ballast gas make-up stream) to produce the EO reactor feed stream 7, wherein at least a portion of the EO reactor feed stream 7 can be subjected to $CO_2$ removal in the $CO_2$ removal system 4 prior to introducing to the EO reactor 2; and wherein the $CO_2$-depleted ODH reactor effluent stream 20 can be recovered from the $CO_2$ removal system 4 and introduced to the EO reactor 2. The $CO_2$ removal system 4 may employ any suitable carbon dioxide removal technology, such as amine, caustic, carbonate-based absorption, and the like, or combinations thereof. The $CO_2$-depleted ODH reactor effluent stream 20 may still contain $CO_2$, although at least 25 mol %, at least 35 mol %, at least 50 mol %, or at least 70 mol % of the $CO_2$ in the ODH reactor effluent stream 6 and/or dehydrated ODH reactor effluent stream is removed in the $CO_2$ removal system 4.

In an aspect, a process for producing EO as disclosed herein can comprise a step of introducing a second reactant mixture (e.g., EO reactor feed stream 7; $CO_2$-depleted ODH reactor effluent stream 20) to the EO reactor 2 to produce a second effluent stream (e.g., EO reactor effluent stream 8); wherein the second reactant mixture comprises at least a portion of the first effluent stream; and wherein the second effluent stream comprises EO, ethane, ethylene, and oxygen.

In some aspects, for example as displayed in the configuration of FIGS. 1-2, the ODH reactor effluent stream 6 and/or dehydrated ODH reactor effluent stream may be combined with one or more streams to produce the EO reactor feed stream 7. For example, the ODH reactor effluent stream 6 and/or dehydrated ODH reactor effluent stream may be combined with a recycle stream (e.g., EO recycle feed stream 15), an EO oxygen make-up feed stream 14, and optionally with a ballast gas make-up stream to produce the EO reactor feed stream 7. EO recycle feed stream 15 has substantially the same composition as the ODH recycle feed stream 16.

In an aspect, the second reactant mixture (e.g., EO reactor feed stream 7; $CO_2$-depleted ODH reactor effluent stream 20) can be characterized by an ethane concentration of less than about 30 mol %, less than about 25 mol %, less than about 20 mol %, less than about 15 mol %, less than about 10 mol %, less than about 9 mol %, less than about 8 mol %, less than about 7 mol %, less than about 6 mol %, less than about 5 mol %, less than about 4 mol %, less than about 3 mol %, less than about 2 mol %, or less than about 1 mol %; from about 0.01 mol % to about 30 mol %, from about 0.01 mol % to about 25 mol %, from about 0.01 mol % to about 20 mol %, from about 0.01 mol % to about 15 mol %, from about 0.01 mol % to about 10 mol %, from about 0.02 mol % to about 9 mol %, from about 0.05 mol % to about 8 mol %, from about 0.06 mol % to about 7 mol %, from about 0.08 mol % to about 6 mol %, from about 0.1 mol % to about 5 mol %, from about 0.1 mol % to about 4 mol %, from about 0.1 mol % to about 3 mol %, from about 0.15 mol % to about 2 mol %, or from about 0.2 mol % to about 1 mol %. In an aspect, the second reactant mixture (e.g., EO reactor feed stream 7; $CO_2$-depleted ODH reactor effluent stream 20) can be characterized by an ethane concentration of less than about 5 mol %, less than about 4 mol %, less than about 3 mol %, less than about 2 mol %, or less than about 1 mol %; from about 0.1 mol % to about 5 mol %, from about 0.1 mol % to about 4 mol %, from about 0.1 mol % to about 3 mol %, from about 0.15 mol % to about 2 mol %, or from about 0.2 mol % to about 1 mol %. In an aspect, the second reactant mixture (e.g., EO reactor feed stream 7; $CO_2$-depleted ODH reactor effluent stream 20) can be characterized by an ethane concentration of less than about 3 mol %, or from about 0.1 mol % to about 3 mol %. For example, the second reactant mixture (e.g., EO reactor feed stream 7; $CO_2$-depleted ODH reactor effluent stream 20) can be characterized by an ethane concentration of less than about 3 mol %, less than about 2 mol %, or less than about 1 mol %; from about 0.1 mol % to about 3 mol %, from about 0.15 mol % to about 2 mol %, or from about 0.2 mol % to about 1 mol %.

In an aspect, the second reactant mixture (e.g., EO reactor feed stream 7; $CO_2$-depleted ODH reactor effluent stream 20) can be characterized by an ethylene concentration of equal to or greater than about 15 mol %, equal to or greater than about 20 mol %, equal to or greater than about 25 mol %, or equal to or greater than about 30 mol %; from about 15 mol % to about 75 mol %, from about 20 mol % to about 70 mol %, from about 25 mol % to about 65 mol %, or from about 30 mol % to about 60 mol %.

In an aspect, supplemental oxygen can be introduced to the EO reactor feed stream 7, in addition to the oxygen introduced to the EO reactor 2 via the EO recycle feed stream 15 and/or via the ODH reactor effluent stream 6. In an aspect, the EO oxygen make-up feed stream 14 can be provided to the EO reactor 2. Stream 14 can be oxygen gas, technical oxygen (which can contain some air), air, oxygen enriched air, and the like, or combinations thereof. In an aspect, stream 14 comprises substantially pure oxygen (e.g., oxygen having less than about 1 vol. % contaminants, such as nitrogen ($N_2$), argon (Ar), etc.). The EO oxygen make-up feed stream 14 provides for supplemental oxygen or fresh oxygen, which replenishes the oxygen that has been consumed (e.g., via ODH reaction in reactor 1, EO reaction in EO reactor 2, combustion reactions in reactors 1 and 2, etc.) and/or lost (e.g., via purge stream 13) in the process.

In an aspect, a ballast gas make-up stream can be provided to the EO reactor 2. In an aspect, the ballast gas make-up stream introduced to the EO reactor 2 comprises methane.

In an aspect, the process for producing EO as disclosed herein can comprise introducing methane to the ODH reactor 1 (e.g., via stream 19, as displayed in the configurations of FIGS. 1-2) and/or the EO reactor 2, wherein streams 10, 12, 13, 15, 7, 16, and 5 are characterized by a methane concentration of equal to or greater than about 20 mol %, equal to or greater than about 25 mol %, equal to or greater than about 30 mol %, equal to or greater than about 35 mol %, or equal to or greater than about 40 mol %; from about 20 mol % to about 80 mol %, from about 25 mol % to about 75 mol %, from about 30 mol % to about 70 mol %, from about 35 mol % to about 65 mol %, or from about 40 mol % to about 60 mol %.

As will be appreciated by one of skill in the art, and with the help of this disclosure, ballast gases may be inert gases introduced with other process feeds that build up in a recycle process. For example, argon and nitrogen may enter with the oxygen and/or ethane feeds to the ODH reactor 1 and/or EO reactor 2 and can build up to appreciable concentrations in the recycle loop (e.g., streams 10, 12, 15, 7, 16, and 5). Ballast gases may be selected for their favorable properties (e.g., thermal performance, chemical inertness), and may also be purposely introduced into the recycle process (i.e., a process for producing EO as disclosed herein). Further, and as will be appreciated by one of skill in the art, and with the help of this disclosure, excess ethane in the EO reactor 2 (i.e., ethane that is not converted in the ODH reactor 1) may also be considered a ballast gas, although it is not fully inert. In some aspects, the ballast gas may comprise atmospheric inerts, methane, ethane, or combinations thereof. Without wishing to be limited by theory, the concentrations of ballast gas components that are established in the recycle loop depend on the rate at which the ballast gas components enter into the process (i.e., feeds to the ODH reactor 1 and/or EO reactor 2) and the flowrate of the purge stream 13 in which the ballast gas components leave the process. While ethane has been previously considered for use as a primary ballast gas in processes integrating ODH and EO, and without wishing to be limited by theory, ethane is not fully inert in the ODH reactor 1 and the EO reactor 2, so allowing ethane to accumulate in the recycle loop leads to loss of ethane due to its reaction with oxygen, which in turn depresses the chemical efficiency of the process. Advantageously, inert gases other than ethane may be used to share the role of ballast gas. For example, if the oxygen feed used as streams 14 and 18 contains about 0.2 mol % argon, and a purge ratio f (f=flowrate of stream 13 divided by the flowrate of streams 10 or 12) is 0.001, argon can accumulate in the recycle loop to a level of greater than about 10 mol %. As another example, when methane is used as ballast gas in stream 19, at a molar flowrate equal to 1.3% of ethane feed stream 17, about 40% methane accumulates in the recycle loop. By employing inert gases other than ethane as the ballast gas, the concentration of ethane can be kept at a reasonable level in the recycle loop, e.g., below about 20 mol %, or below about 10 mol %.

The EO reactor 2 can be any suitable reactor, such as a continuous flow reactor, a fixed bed reactor, a fluidized bed reactor, a multi-tubular reactor, and the like, or combinations thereof. In an aspect, the ODH reactor 1 comprises a continuous flow multi-tubular reactor, wherein the tubes contain an EO catalyst, and wherein a cooling medium contacting an outer surface of the tubes provides for temperature control of the EO reactor.

In an aspect, the EO reactor 2 can be characterized by an EO reactor operating temperature of from about 100° C. to about 400° C., from about 150° C. to about 350° C., or from about 200° C. to about 300° C. The EO reactor operating temperature is defined as the average of EO reactor inlet temperature and EO reactor outlet temperature.

In an aspect, the EO reactor 2 can be characterized by an EO reactor operating pressure of from about 1 barg to about 35 barg, from about 3 barg to about 30 barg, from about 5 barg to about 25 barg, or from about 10 barg to about 20 barg.

In an aspect, the EO reactor 2 comprises an EO catalyst. The EO catalyst comprises any EO catalyst suitable for catalyzing an EO reaction. For example, the EO catalyst can comprise silver. In an aspect, the EO catalyst comprises silver oxide. The EO catalyst may further comprise a promoter, such as rhenium, tungsten, molybdenum, chromium, and the like, or combinations thereof.

In an aspect, a moderator can be further introduced to the EO reactor 2. Generally, a moderator may be introduced to EO reactors comprising an EO catalyst for catalyst performance control. Nonlimiting examples of moderators suitable for use in the EO reactor as disclosed herein include a chlorohydrocarbon, ethyl chloride, vinyl chloride, dichloroethane, ethylene dichloride, and the like, or combinations thereof. In an aspect, the moderator comprises ethyl chloride. The moderator may be present in the EO reactor feed stream 7 in an amount of from about 1 part per million volume (ppmv) to about 2,000 ppmv, based on the total volume of the EO reactor feed stream 7. The EO reactor, EO catalyst, and EO operating conditions (e.g., pressure, temperature, moderator) are described in more detail in U.S. Pat. Nos. 8,148,555; and 9,649,621; each of which is incorporated by reference herein in its entirety.

The ethylene introduced to the EO reactor 2 contacts the EO catalyst and, in the presence of oxygen, is converted to EO via the EO reaction (2):

$$C_2H_4 + \tfrac{1}{2}O_2 \rightarrow C_2H_4O \qquad (2)$$

Several side reactions (i.e., reactions other than ethylene conversion to EO via EO reaction (2)) may occur in the EO reactor 2, such as CO oxidation to $CO_2$. Further, a portion of ethane, a portion of ethylene, a portion of acetic acid, a portion of acetylene, or combinations thereof in the EO reactor 2 can combust in the presence of oxygen to produce $CO_2$, and water.

The EO reactor effluent stream 8 can be recovered from the EO reactor 2, wherein the EO reactor effluent stream 8 can comprise EO, ethylene, ethane, oxygen, carbon dioxide, and water. The EO reactor effluent stream 8 can further comprise a ballast gas (e.g., methane) and/or a moderator. In an aspect, ethylene is not separated from the EO reactor effluent stream 8; i.e., ethylene is not separated from the ethane in the EO reactor effluent stream 8, prior to recycling the ethylene in the EO reactor effluent stream 8 to the ODH reactor 1 and EO reactor 2.

In an aspect, a process for producing EO as disclosed herein can comprise a step of separating at least a portion of the second effluent stream (e.g., EO reactor effluent stream 8) into an EO product stream (e.g., EO product stream 9) and a recycle stream (e.g., EO-depleted product stream 10; $CO_2$-depleted stream 12); wherein the EO product stream comprises at least a portion of the EO in the second effluent stream; and wherein the recycle stream comprises ethane, ethylene, and oxygen.

In an aspect, at least a portion of the EO reactor effluent stream 8 can be introduced to the product recovery system 3 to produce the EO product stream 9 and the EO-depleted product stream 10; wherein the EO product stream 9 comprises EO and water, and wherein the EO-depleted product stream 10 comprises ethylene, ethane, oxygen, and carbon dioxide. The product recovery system 3 may employ condensation (e.g., lowering the stream temperature to promote condensation); a series of absorption and stripping columns; etc.

In some aspects, and referring to the configuration of FIG. 1, the EO-depleted product stream 10 can be introduced to the $CO_2$ removal system 4 to yield $CO_2$-depleted stream 12 and $CO_2$-containing stream 11. The $CO_2$-containing stream 11 can comprise at least 25 mol %, at least 35 mol %, at least 50 mol %, or at least 70 mol % of the $CO_2$ in the EO-depleted product stream 10. The $CO_2$-depleted stream 12 comprises ethylene, ethane, and oxygen; and optionally $CO_2$ (i.e., the $CO_2$ that has not been removed into $CO_2$-containing stream 11).

In an aspect, the recycle stream (e.g., EO-depleted product stream 10; CO$_2$-depleted stream 12) can be characterized by a combined concentration of ethane and ethylene of less than about 60 mol %, less than about 55 mol %, less than about 50 mol %, less than about 45 mol %, less than about 40 mol %, less than about 35 mol %, less than about 30 mol %, or less than about 25 mol %; from about 15 mol % to about 60 mol %, from about 15 mol % to about 55 mol %, from about 15 mol % to about 50 mol %, from about 18 mol % to about 45 mol %, from about 19 mol % to about 40 mol %, from about 20 mol % to about 35 mol %, from about 20 mol % to about 30 mol %, or from about 20 mol % to about 25 mol %.

In an aspect, the recycle stream (e.g., EO-depleted product stream 10; CO$_2$-depleted stream 12) can be characterized by an ethane concentration of less than about 30 mol %, less than about 25 mol %, less than about 20 mol %, less than about 15 mol %, less than about 10 mol %, less than about 9 mol %, less than about 8 mol %, less than about 7 mol %, less than about 6 mol %, less than about 5 mol %, less than about 4 mol %, less than about 3 mol %, less than about 2 mol %, or less than about 1 mol %; from about 0.01 mol % to about 30 mol %, from about 0.01 mol % to about 25 mol %, from about 0.01 mol % to about 20 mol %, from about 0.01 mol % to about 15 mol %, from about 0.01 mol % to about 10 mol %, from about 0.02 mol % to about 9 mol %, from about 0.05 mol % to about 8 mol %, from about 0.06 mol % to about 7 mol %, from about 0.08 mol % to about 6 mol %, from about 0.1 mol % to about 5 mol %, from about 0.1 mol % to about 4 mol %, from about 0.1 mol % to about 3 mol %, from about 0.15 mol % to about 2 mol %, or from about 0.2 mol % to about 1 mol %.

In an aspect, a purge stream 13 can be withdrawn from the EO-depleted product stream 10 and/or the CO$_2$-depleted stream 12, or from any other suitable stream in the recycle loop comprising units 1, 2, 3, and 4 in FIGS. 1-2, to avoid build-up of inerts in the recycle loop. A purge ratio (f) is defined as the volumetric flow rate of the purge stream 13 divided by the flow rate of the stream(s) it was withdrawn from (e.g., divided by the volumetric flow rate of the EO-depleted product stream 10 and/or the CO$_2$-depleted stream 12, respectively). In an aspect, the purge ratio can be from about 0.0001 to about 0.005, from about 0.0002 to about 0.003, or from about 0.0003 to about 0.002.

In an aspect, a process for producing EO as disclosed herein can comprise a step of recycling a first portion of the recycle stream (e.g., EO-depleted product stream 10; CO$_2$-depleted stream 12) to the ODH reactor 1 (e.g., via ODH reactor feed stream 5), and a second portion of the recycle stream to the EO reactor 2 (e.g., via EO reactor feed stream 7). In such aspect, a recycle split ratio (a) can be less than about 0.9, less than about 0.8, less than about 0.7, less than about 0.6, less than about 0.5, less than about 0.45, less than about 0.4, less than about 0.35, less than about 0.3, less than about 0.25, or less than about 0.2, from about 0.1 to about 0.9, from about 0.2 to about 0.9, from about 0.25 to about 0.9, from about 0.2 to about 0.6, from about 0.3 to about 0.6, or from about 0.25 to about 0.45; wherein the recycle split ratio is defined as the ratio of the volumetric flowrate of the first portion of the recycle stream divided by the sum of the volumetric flowrate of the first portion of the recycle stream and the volumetric flowrate of the second portion of the recycle stream. In an aspect, the recycle split ratio can be less than about 0.6; or from about 0.2 to about 0.6.

Purge stream 13 is withdrawn from the recycle stream (e.g., EO-depleted product stream 10; CO$_2$-depleted stream 12), and the remainder of the recycle stream is split into the EO recycle feed stream 15 (e.g., a second portion of the recycle stream) and the ODH recycle feed stream 16 (e.g., a first portion of the recycle stream). As disclosed herein, the EO recycle feed stream 15 (e.g., a second portion of the recycle stream) and the ODH recycle feed stream 16 (e.g., a first portion of the recycle stream) are recycled to the EO reactor 2 and the ODH reactor 1, respectively without separating ethane from ethylene in the EO recycle feed stream 15 and the ODH recycle feed stream 16, respectively. As will be appreciated by one of skill in the art, and with the help of this disclosure, owing to relatively low conversions of ethylene in the EO reactors, processes for the production of EO generally operate at high recycle ratios (i.e., the flowrate of EO reactor feed stream is about 25-50 times the flowrate of fresh ethylene (in the case of a stand-alone EO process) or fresh ethane (in the case of an EO process integrated with ODH)), and thus conventional processes may separate the ethane from ethylene for recycling purposes. However, the process for producing EO as disclosed herein advantageously excludes the separation of ethane from ethylene from recycle streams (e.g., EO-depleted product stream 10; CO$_2$-depleted stream 12; EO recycle feed stream 15; ODH recycle feed stream 16).

In an aspect, a process for producing EO as disclosed herein can advantageously display improvements in one or more process characteristics when compared to conventional processes for the production of EO.

In an aspect, the EO in the EO product stream 9 can be further used as a chemical intermediate, for example for conversion to ethylene glycol and its derivatives.

In an aspect, a process for producing EO as disclosed herein can employ operating conditions for both the ODH and EO reactors that can be advantageously selected to optimize process performance. The EO reactor 2 may be operated with similar conditions (e.g., feed composition, pressure, inlet temperature, and coolant temperature) and similar design (e.g., including choice of catalyst) as in conventional EO processes. Alternatively, the EO reactor 2 may be operated at a different ethylene concentration in the inlet; for example, instead of the conventional concentration of 30-35% ethylene in the feed, somewhat lower ethylene concentrations, e.g., of 15-30%, or 15-25% may be advantageously employed in the EO reactor feed stream 7 under certain circumstances. The operating conditions for the ODH reactor 1 may be selected to ensure process safety (which imposes a limit on the inlet concentration of oxygen, as well as the inlet and coolant temperatures) while maximizing reactor performance and optimizing reactor size. In an aspect, both the ODH reactor 1 and the EO reactor 2 can be operated with oxygen concentrations in their respective feed close to their maximum respective safe values, by advantageously maintaining separate oxygen make-up flows to each reactor.

In an aspect, as the recycle flow to the ODH reactor 1 decreases, and assuming the oxygen concentration in the ODH feed is maintained at the maximum safe level to avoid flammable conditions, the fractional conversion of oxygen through the ODH reactor 1 must increase in order to convert the required amount of ethane (i.e., close to the amount of fresh ethane fed to the ODH reactor 1). The ODH reactor may be advantageously operated at an oxygen conversion greater than about 30%, greater than about 45%, or greater than about 60%; from about 30% to about 100%, from about 45% to about 100%, from about 45% to about 99%, or from about 60% to about 97.5%.

In an aspect, a process for producing EO as disclosed herein can advantageously provide for adjusting the concentration of ethylene in the recycle loop by adjusting the recycle split ratio. For example, the concentration of ethylene in the recycle loop may be adjusted upward by increasing the recycle split ratio, and downward by decreasing the recycle split ratio. The ability to adjust the concentration of ethylene in the recycle loop by adjusting the recycle split ratio advantageously provides a measure of control that can be used to optimize the process for producing EO as disclosed herein, which control measure is not available in conventional process configurations that lack the split recycle concept. This control measure may be used in conjunction with controlling the purge ratio and the flow of make-up ballast gas, to establish reactor feed compositions most conducive to high process performance (e.g., process productivity and/or selectivity).

In an aspect, a process for producing EO as disclosed herein can comprise a step of determining a molar concentration of ethylene in the recycle stream. For purposes of the disclosure herein, the step of determining a molar concentration of ethylene in the recycle stream encompasses determining the molar concentration of ethylene at any suitable point in the recycle loop (e.g., streams 10, 12, 13, 15, 7, 16, and 5); such as determining the ethylene concentration in stream 10, stream 12, stream 13, stream 15, stream 7, stream 16, stream 5, and the like, or combinations thereof. For example, a process analyzer may provide continuous or periodic analysis of the recycle stream composition, or the composition of the feed to the EO reactor 2.

In an aspect, a process for producing EO as disclosed herein can comprise a step of comparing the molar concentration of ethylene in the recycle stream with a target molar concentration of ethylene in the recycle stream. Responsive to the step of comparing the molar concentration of ethylene in the recycle stream with a target molar concentration of ethylene in the recycle stream, when the molar concentration of ethylene in the recycle stream is less than the target molar concentration of ethylene in the recycle stream, the recycle split ratio can be increased. In other words, if the concentration of ethylene in the recycle stream is below the value at which the most favorable process performance is attained, the recycle split ratio can be increased. Responsive to the step of comparing the molar concentration of ethylene in the recycle stream with a target molar concentration of ethylene in the recycle stream, when the molar concentration of ethylene in the recycle stream is greater than the target molar concentration of ethylene in the recycle stream, the recycle split ratio can be decreased. In other words, if the concentration of ethylene in the recycle stream is above the value at which the most favorable process performance is attained, the recycle split ratio can be decreased. In an aspect, the recycle split ratio can be modified to be in a range of from about 0.2 to about 0.8, or from about 0.2 to about 0.6.

In an aspect, the target molar concentration of ethylene in the recycle stream can be from about 25 mol % to about 40 mol %, from about 27 mol % to about 37 mol %, or from about 30 mol % to about 35 mol %.

In an aspect, a process for producing EO as disclosed herein can be advantageously characterized by an amount of EO in the EO product stream 9 that is greater than an amount of EO produced in an otherwise similar process that is characterized by a molar concentration of ethylene in the recycle stream different than the target molar concentration of ethylene in the recycle stream of from about 25 mol % to about 40 mol % (e.g., below 25 mol % or above 40 mol %).

In some aspects, adjusting the recycle split ratio, and depending on the configuration of process equipment, may involve incrementally opening or closing a flow control valve, or adjusting the operating parameters of a recycle compressor. The results from the same process analysis may also be used to adjust the purge flow rate (for example, to increase purge flow rate when the concentration of atmospheric inerts becomes higher than desired) and/or the makeup ballast gas flow rate (for example, to decrease the makeup ballast gas flow rate when the concentration of the ballast gas, e.g. methane, exceeds the desired value).

In an aspect, a process for producing EO as disclosed herein can employ ODH catalysts, EO catalysts, and moderators as previously described herein. Without wishing to be limited by theory, ideally, the ODH catalyst in the ODH reactor 1 would only act on ethane, and would not convert ethylene; and likewise, under ideal assumptions, the EO catalyst in the EO reactor 2 would only act on ethylene, and would not convert ethane. In reality, some small fractional conversion of these compounds (ethylene in the ODH reactor 1; ethane in the EO reactor 2) may take place over the catalysts employed; and these fractional conversions may be referred to as "parasitic" conversions, which are the result of parasitic reactions (e.g., unwanted reactions). The process for producing EO as disclosed herein advantageously gives rise to relatively low-level parasitic conversions, which in turn leads to improved process characteristics (e.g., relatively high EO yield). As will be described in more detail in the Examples later herein, relatively low-level parasitic conversions can be accomplished by minimizing the concentration of ethane in the recycle streams and/or by selecting an appropriately low value of the recycle split to the ODH reactor 1. In an aspect, a process for producing EO as disclosed herein can advantageously provide for reducing the operating cost of the ODH reactor 1.

In an aspect, a process for producing EO as disclosed herein can advantageously provide for a relatively high ethylene oxide yield, while balancing the competing objective of low equipment cost. Ethylene oxide yield (defined as the molar fraction of the fresh feed of ethane that is converted (in the sequence of ODH and EO reactors) to the EO product) is the most important parameter affecting the operating cost of EO production. The practical value (as opposed to the theoretical value) is smaller than 100%, owing to imperfect selectivity towards desired products in the ODH and EO reactors, ethane and ethylene losses in purge stream(s), and in some cases parasitic conversion of ethane in the EO reactor and/or ethylene in the ODH reactor. In a process integrating ODH and EO for EO production, such as the process for producing EO as disclosed herein, the cost of ODH and EO reactors can represent a large fraction of the equipment cost, since expensive cryogenic separation of ethylene from ethane in the recycle loop is advantageously avoided. In an aspect, a process for producing EO as disclosed herein can advantageously provide for optimizing reactor size and cost. Additional advantages of the process for producing EO as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example

The data encompass novel process configurations for integrating ODH and EO as examined by process and reactor modeling and simulation. The integrated ODH and EO process was modeled using Aspen Plus process simulation software, based on the EO production system 100 displayed in FIG. 1. The ODH reactor was characterized by an ethylene carbon molar selectivity of 95%, a CO carbon molar selectivity of 2.5%, and a $CO_2$ carbon molar selectivity of 2.5%. An upper limit concentration of 8.5% oxygen was imposed on the feed to the ODH reactor to avoid explosive conditions. The ODH reactor was modeled as a multi-tubular packed bed reactor in which the conversion of ethane was selected to achieve mass balance of ethane (i.e., the rate of conversion of ethane in the ODH reactor plus losses of ethane elsewhere in the system matched the feed rate of fresh ethane). The EO reactor was characterized by an ethylene oxide carbon molar selectivity of 84% and a $CO_2$ carbon molar selectivity of 16%. The oxygen concentration in the feed to the EO reactor was maintained at 9.1%, and the oxygen conversion was taken to be 30% in the EO reactor, representative of conventional EO processes. The model also accounted for conversion of 50% of the CO in the EO reactor feed to $CO_2$. To allow for meaningful comparison among cases studied, the ethylene concentration in the EO reactor feed was maintained at 34.5% for all cases (by selecting appropriate values for the free parameters). The recovery of EO from the EO reactor effluent was modeled as 100% efficient, while 40% $CO_2$ removal efficiency was modeled for the $CO_2$ removal unit. The ethane feed stream was taken to be 100% ethane, while the oxygen feed contained 0.2% argon. When make-up ballast gas was included in the calculations, methane was used as makeup ballast gas; parameter b represents the ballast gas make-up molar flowrate divided by the molar flowrate of the fresh ethane feed stream. The model calculations were conducted for several combinations of the process parameters (purge ratio f; recycle split ratio a; ballast gas make-up b). The calculations were performed using assumptions of ideal chemistry, and also using small assumed losses of ethane and/or ethylene due to their parasitic conversion. Parameter $z_{C2H6}$ represents the fractional conversion of ethane in the EO reactor, to form combustion products $CO_2$ and water. Parameter $z_{C2H4}$ represents the fractional conversion of ethylene in the ODH reactor, to form combustion products $CO_2$ and water. The results (Examples 1-14b) are shown in Table 1 below, in which the EO yield $Y_{EO}$ is the molar flowrate of EO in the EO product stream divided by the molar flowrate of the fresh ethane feed stream; the EO recycle ratio $RR_{EO}$ is the molar flowrate of the EO reactor feed stream divided by the molar flowrate of ethane in the fresh ethane feed stream; and the ODH recycle ratio $RR_{ODH}$ is the molar flowrate of the ODH reactor feed stream divided by the molar flowrate of ethane in the fresh ethane feed stream. The conversion of oxygen through the ODH reactor ($x_{O2,ODH}$) and the mole fraction of ethylene in the EO reactor feed ($y_{C2H4,EOin}$) are also shown in Table 1.

TABLE 1

| Example # | $z_{C2H4}$ | $z_{C2H6}$ | $f_{purge}$ | a | b | $Y_{EO}$ | $RR_{ODH}$ | $RR_{EO}$ | $x_{O2, ODH}$ | $y_{C2H4, EOin}$ |
|---|---|---|---|---|---|---|---|---|---|---|
| 1 | 0 | 0 | 0.003 | 0.282 | 0 | 0.737 | 8.92 | 28.97 | 79.0% | 34.5% |
| 2 | 0 | 0 | 0.001 | 0.277 | 0 | 0.776 | 9.20 | 30.48 | 79.0% | 34.5% |
| 3 | 0 | 0 | 0.0003 | 0.275 | 0 | 0.790 | 9.30 | 31.05 | 79.0% | 34.5% |
| 4 | 0 | 0 | 0.001 | 0.278 | 0.0137 | 0.786 | 9.33 | 30.86 | 79.0% | 34.5% |
| 5 | 0 | 0 | 0.001 | 0.214 | 0.0135 | 0.786 | 7.44 | 30.87 | 99.0% | 34.5% |
| 6 | 0 | 0 | 0.001 | 0.391 | 0.0135 | 0.785 | 12.69 | 30.86 | 58.0% | 34.5% |
| 7 | 0 | 0 | 0.001 | 0.669 | 0.0135 | 0.785 | 21.01 | 30.85 | 35.0% | 34.5% |
| 8 | 0 | 0 | 0.001 | 0.989 | 0.014 | 0.785 | 30.64 | 30.84 | 24.0% | 34.5% |
| 9 | 0.01 | 0 | 0.001 | 0.286 | 0.0135 | 0.763 | 9.33 | 29.98 | 79.0% | 34.5% |
| 10 | 0.01 | 0 | 0.001 | 0.990 | 0.0112 | 0.713 | 27.79 | 28.01 | 26.5% | 34.5% |
| 11 | 0 | 0.01 | 0.001 | 0.274 | 0 | 0.698 | 8.28 | 27.42 | 79.0% | 34.5% |
| 12 | 0 | 0.01 | 0.001 | 0.277 | 0.0135 | 0.781 | 9.27 | 30.68 | 79.0% | 34.5% |
| 13 | 0 | 0.01 | 0.001 | 0.980 | 0.0135 | 0.778 | 30.11 | 30.56 | 24.2% | 34.5% |
| 14 | 0.01 | 0.01 | 0.001 | 0.286 | 0.0125 | 0.757 | 9.26 | 29.77 | 79.0% | 34.5% |
| 15 | 0.01 | 0.01 | 0.001 | 0.990 | 0.011 | 0.707 | 27.58 | 27.79 | 26.5% | 34.5% |
| 14a | 0.01 | 0.01 | 0.001 | 0.285 | 0.0125 | 0.756 | 9.20 | 29.69 | 79.0% | 32.3% |
| 14b | 0.01 | 0.01 | 0.001 | 0.287 | 0.0125 | 0.760 | 9.31 | 29.86 | 79.0% | 36.3% |

The maximum value of EO yield, given the selectivities to ethylene and EO in the two reactors, is 0.798. Examples 1-3 in Table 1 show that this maximum selectivity value may be approached in the case where ethane is not parasitically converted in the process, by selecting a very low value of the purge ratio f. The accumulation of atmospheric inerts and other contaminants in the recycle loop, which may affect reactor operation, poses practical limitations on reducing the purge ratio. An f value of 0.001 is consistent with current industrial practice, and is therefore used in further examples. Thus, operating without on-purpose methane as ballast gas results in Example 2 with an EO yield of 0.776, a few percent below the maximum value; wherein the yield loss can be attributed to purge losses. Example 4 shows that the yield can be improved by introducing methane as a ballast gas, thereby suppressing the concentration of ethane in the recycle loop.

Examples 4-8 demonstrate that if no adverse chemistry occurs ($z_{C2H4}$ and $z_{C2H6}$ are zero), high yields may be attained at different values of parameter a, ranging from a small fractional recycle (a=0.29) to nearly full recycle to the ODH reactor (a=0.99). However, the magnitude of the ODH recycle ratio $RR_{ODH}$ increases as a increases, and becomes quite large at full recycle; a reactor built to accommodate the corresponding high flowrate would be large compared to the reactor for a process with smaller value of a, so it is beneficial to select a value for a that is lower than one. As the value of a decreases, the fractional conversion of oxygen through the ODH reactor increases. Practical values for a range from a maximum of 1 to a minimum set by the need to convert sufficient ethane in the ODH reactor to meet process performance. For the process conditions modeled here, this minimum value for a is 0.22; at this value, the conversion of oxygen through the ODH reactor is complete. The economic optimum is not necessarily obtained at the minimum value for a; other considerations, such as reaction kinetics, also affect the equipment cost. In practice, intermediate values of a, for example from 0.25 to 0.9, or from 0.3 to 0.6, may result in the economically most attractive process.

Examples 9 and 10 demonstrate that the effect of parasitic conversion of ethylene in the ODH reactor on EO yield is much greater for full recycle (large a value) than for minimal recycle (small a value), which provides further incentive to reduce the recycle split ratio to a value well below one.

Example 11 demonstrates that even a small parasitic conversion of ethane in the EO reactor can significantly affect the EO yield if no measures are taken to suppress the concentration of ethane in the recycle loop. Examples 12 and 13 illustrate that the introduction of methane as ballast gas greatly reduces the EO yield loss; and the same could be accomplished with a lower purge rate, by allowing more argon to build up in the recycle loop.

Examples 14 and 15 demonstrate that even when both ethane and ethylene are lost to parasitic conversion in the reactors, the extent of EO yield loss can be limited to a reasonable level if a sufficiently small value of a is selected, along with values of b and $f_{purge}$ suitable to limit ethane accumulation in the recycle loop.

Examples 14a and 14b, in conjunction with Example 14, show how a slight adjustment of the recycle split ratio results in a corresponding change in the ethylene mole fraction in the EO reactor feed. This demonstrates how the recycle split ratio may be used to control the composition of ethylene in the recycle loop to its desired value. It should be noted that the results in the examples correspond to steady-state operation; in industrial practice, the response will be a dynamic one, such that the loop concentrations gradually approach the desired value. A thorough understanding of the process dynamics, such as may be gained from process simulation, will aid in configuring a stable and dependable control scheme. In examples 14, 14a, and 14b, the fractional conversion of oxygen in the ODH reactor is assumed to stay the same as the flow through the ODH reactor is varied. This might be achieved in practice through slight adjustments to the reactor operating temperature by any suitable means. Alternatively, the fractional oxygen conversion can be left to find its own new steady-state value at the same reactor conditions; and in this case, the response factor (fractional change in ethylene concentration divided by fractional change in recycle split ratio) will be smaller, but still positive, so the control scheme can be successful in this case as well.

In conclusion, these results demonstrate that, even in the absence of a costly ethylene/ethane separation step in the recycle process, and even if undesired process chemistry leads to parasitic loss of ethane and/or ethylene, very good process performance can be attained, with EO yields only marginally lower than the maximum EO yield—but only by carrying out the process with a recycle split ratio at a suitably low value, e.g. less than 0.6, less than 0.45, or less than 0.3; or from about 0.2 to about 0.6; and/or oxygen conversions through the ODH reactor of greater than 30%, greater than 45%, or greater than 60%; from about 30% to about 100%, from about 45% to about 100%, from about 45% to about 99%, or from about 60% to about 97.5%. Such high conversions are not obvious; the selective oxidation of ethylene to EO (carried out in a similar type of reactor with similar operating conditions), for example, is commonly carried out with ethylene conversion levels much smaller than 30%. Moreover, the results in Table 1 show how the composition of the EO reactor feed can be suitably adjusted to the desired value by varying the recycle split ratio during operation.

The results in Table 1 surprisingly display that the ODH reactor process does not require as large a recycle ratio as the EO process, even though both reactors are selective partial oxidation reactors operating at similar temperature and pressure ranges with similar concentrations of oxygen in the feed. For example, an ODH recycle ratio (ratio of stream 16 to stream 5) of 8-20 may suffice. Advantageously, the recycle split ratio a can be selected to operate the ODH reactor with desired performance, without requiring an excessively large reactor. In some aspects, the recycle split ratio may be advantageously set at a value in the range from 0.25 to 0.9, or from 0.3 to 0.6.

Additional Disclosure

A first embodiment, which is an ethylene oxide (EO) production process comprising: (a) introducing a first reactant mixture to a first reactor to produce a first effluent stream; wherein the first reactant mixture comprises ethane, and oxygen; and wherein the first effluent stream comprises ethylene, ethane, and oxygen; (b) introducing a second reactant mixture to a second reactor to produce a second effluent stream; wherein the second reactant mixture comprises at least a portion of the first effluent stream; wherein ethylene is not separated from the first effluent stream; and wherein the second effluent stream comprises EO, ethane, ethylene, and oxygen; (c) separating at least a portion of the second effluent stream into an EO product stream and a recycle stream; wherein the EO product stream comprises at least a portion of the EO in the second effluent stream; and wherein the recycle stream comprises ethane, ethylene, and oxygen; and (d) recycling a first portion of the recycle stream to the first reactor in step (a), and a second portion of the recycle stream to the second reactor in step (b); wherein ethylene is not separated from the recycle stream; wherein a recycle split ratio is from about 0.2 to about 0.6; and wherein the recycle split ratio is defined as the ratio of the volumetric flowrate of the first portion of the recycle stream divided by the sum of the volumetric flowrate of the first portion of the recycle stream and the volumetric flowrate of the second portion of the recycle stream.

A second embodiment, which is the process of the first embodiment, wherein the first reactor is characterized by an oxygen conversion of from about 30% to about 100%.

A third embodiment, which is the process of any of the first and the second embodiments, wherein the first effluent stream is characterized by an ethane concentration of from about 0.1 mol % to about 5 mol %.

A fourth embodiment, which is the process of any of the first through the third embodiments, wherein the recycle stream is characterized by an ethane concentration of from about 0.1 mol % to about 5 mol %.

A fifth embodiment, which is the process of any of the first through the fourth embodiments, wherein a concentration of ethane in the second reactant mixture and/or the recycle stream is from about 0.1 mol % to about 3 mol %.

A sixth embodiment, which is the process of any of the first through the fifth embodiments further comprising withdrawing a third portion of the recycle stream as a purge stream; wherein the purge stream is characterized by a purge ratio of from about 0.0001 to about 0.005; and wherein the purge ratio is defined as the ratio of the volumetric flowrate of the purge stream divided by the volumetric flowrate of the recycle stream.

A seventh embodiment, which is the process of any of the first through the sixth embodiments further comprising introducing methane to the first reactor and/or the second reactor, wherein the recycle stream is characterized by a methane concentration of from about 20 mol % to about 80 mol %.

An eighth embodiment, which is the process of any of the first through the seventh embodiments, wherein the recycle stream is characterized by a combined concentration of ethane and ethylene from about 15 mol % to about 50 mol %.

A ninth embodiment, which is the process of any of the first through the eighth embodiments, wherein supplemental oxygen is introduced to the first reaction mixture, in addition to the oxygen recycled to the first reactor via the first portion of the recycle stream.

A tenth embodiment, which is the process of any of the first through the ninth embodiments, wherein supplemental oxygen is introduced to the second reaction mixture, in addition to the oxygen introduced to the second reactor via the second portion of the recycle stream and/or via the first effluent stream.

An eleventh embodiment, which is the process of any of the first through the tenth embodiments, wherein the recycle split ratio is less than about 0.45.

A twelfth embodiment, which is the process of any of the first through the eleventh embodiments, wherein the recycle split ratio is less than about 0.3.

A thirteenth embodiment, which is the process of any of the first through the twelfth embodiments, wherein the first reactor is characterized by an ethane conversion of from about 60% to about 100%.

A fourteenth embodiment, which is the process of any of the first through the thirteenth embodiments, wherein the first reactant mixture is characterized by a molar ratio of ethylene to ethane of from about 1.3 to about 3.0.

A fifteenth embodiment, which is the process of any of the first through the fourteenth embodiments, wherein the first effluent stream, the second effluent stream, and the recycle stream comprise carbon dioxide; and wherein (i) at least a portion of the carbon dioxide is removed from the first effluent stream prior to feeding the first effluent stream to the second reactor in step (b); and/or (ii) at least a portion of the carbon dioxide is removed from the recycle stream prior to the step (d) of recycling a first portion of the recycle stream to the first reactor in step (a), and a second portion of the recycle stream to the second reactor in step (b).

A sixteenth embodiment, which is an ethylene oxide (EO) production process comprising: (a) introducing a first reactant mixture to an oxidative dehydrogenation (ODH) reactor to produce a first effluent stream; wherein the first reactant mixture comprises ethane, and oxygen; and wherein the first effluent stream comprises ethylene, ethane, and oxygen; (b) introducing a second reactant mixture to an EO reactor to produce a second effluent stream; wherein the second reactant mixture comprises at least a portion of the first effluent stream; wherein ethylene is not separated from the first effluent stream; and wherein the second effluent stream comprises EO, ethane, ethylene, oxygen, and carbon dioxide; (c) separating at least a portion of the second effluent stream into an EO product stream and a recycle stream; wherein the EO product stream comprises at least a portion of the EO in the second effluent stream; wherein the recycle stream comprises ethane, ethylene, oxygen, and carbon dioxide; and wherein at least a portion of the carbon dioxide is optionally removed from the recycle stream; (d) recycling a first portion of the recycle stream to the ODH reactor in step (a), and a second portion of the recycle stream to the EO reactor in step (b); wherein ethylene is not separated from the recycle stream; wherein a recycle split ratio is defined as the ratio of the volumetric flowrate of the first portion of the recycle stream divided by the sum of the volumetric flowrate of the first portion of the recycle stream and the volumetric flowrate of the second portion of the recycle stream; (e) determining a molar concentration of ethylene in the recycle stream; (f) comparing the molar concentration of ethylene in the recycle stream with a target molar concentration of ethylene in the recycle stream; (g) responsive to step (f), when the molar concentration of ethylene in the recycle stream is less than the target molar concentration of ethylene in the recycle stream, increasing the recycle split ratio; and (h) responsive to step (f), when the molar concentration of ethylene in the recycle stream is greater than the target molar concentration of ethylene in the recycle stream, decreasing the recycle split ratio.

A seventeenth embodiment, which is the process of the sixteenth embodiment, wherein the target molar concentration of ethylene in the recycle stream is from about 25 mol % to about 40 mol %.

An eighteenth embodiment, which is the process of any of the sixteenth and the seventeenth embodiments, wherein a concentration of ethane in the second reactant mixture and/or the recycle stream is from about 0.1 mol % to about 3 mol %.

A nineteenth embodiment, which is the process of any of the sixteenth through the eighteenth embodiments, wherein the ODH reactor is characterized by an ethane conversion of from about 70% to about 100%.

A twentieth embodiment, which is the process of any of the sixteenth through the nineteenth embodiments, wherein the recycle split ratio is modified to be in a range of from about 0.2 to about 0.6.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. An ethylene oxide (EO) production process comprising:
   (a) introducing a first reactant mixture to a first reactor to produce a first effluent stream; wherein the first reactant mixture comprises ethane, and oxygen; and wherein the first effluent stream comprises ethylene, ethane, and oxygen;
   (b) introducing a second reactant mixture to a second reactor to produce a second effluent stream; wherein the second reactant mixture comprises at least a portion of the first effluent stream; wherein ethylene is not separated from the first effluent stream; and wherein the second effluent stream comprises EO, ethane, ethylene, and oxygen;
   (c) separating at least a portion of the second effluent stream into an EO product stream and a recycle stream; wherein the EO product stream comprises at least a portion of the EO in the second effluent stream; and wherein the recycle stream comprises ethane, ethylene, and oxygen; and
   (d) recycling a first portion of the recycle stream to the first reactor in step (a), and a second portion of the recycle stream to the second reactor in step (b); wherein ethylene is not separated from the recycle stream; wherein a recycle split ratio is from about 0.2 to about 0.6, wherein the recycle split ratio is defined as the ratio of the volumetric flowrate of the first portion of the recycle stream divided by the sum of the volumetric flowrate of the first portion of the recycle stream and the volumetric flowrate of the second portion of the recycle stream; and wherein the first portion and the second portion have a same composition.

2. The process of claim 1, wherein the first reactor is characterized by an oxygen conversion of from about 30% to about 100%.

3. The process of claim 1, wherein the first effluent stream is characterized by an ethane concentration of from about 0.1 mol % to about 5 mol %.

4. The process of claim 1, wherein the recycle stream is characterized by an ethane concentration of from about 0.1 mol % to about 5 mol %.

5. The process of claim 1, wherein a concentration of ethane in the second reactant mixture and/or the recycle stream is from about 0.1 mol % to about 3 mol %.

6. The process of claim 1 further comprising withdrawing a third portion of the recycle stream as a purge stream; wherein the purge stream is characterized by a purge ratio of from about 0.0001 to about 0.005; and wherein the purge ratio is defined as the ratio of the volumetric flowrate of the purge stream divided by the volumetric flowrate of the recycle stream.

7. The process of claim 1 further comprising introducing methane to the first reactor and/or the second reactor, wherein the recycle stream is characterized by a methane concentration of from about 20 mol % to about 80 mol %.

8. The process of claim 1, wherein the recycle stream is characterized by a combined concentration of ethane and ethylene from about 15 mol % to about 50 mol %.

9. The process of claim 1, wherein supplemental oxygen is introduced to the first reaction mixture, in addition to the oxygen recycled to the first reactor via the first portion of the recycle stream.

10. The process of claim 1, wherein supplemental oxygen is introduced to the second reaction mixture, in addition to the oxygen introduced to the second reactor via the second portion of the recycle stream and/or via the first effluent stream.

11. The process of claim 1, wherein the recycle split ratio is less than about 0.45.

12. The process of claim 1, wherein the recycle split ratio is less than about 0.3.

13. The process of claim 1, wherein the first reactor is characterized by an ethane conversion of from about 60% to about 100%.

14. The process of claim 1, wherein the first reactant mixture is characterized by a molar ratio of ethylene to ethane of from about 1.3 to about 3.0.

15. The process of claim 1, wherein the first effluent stream, the second effluent stream, and the recycle stream comprise carbon dioxide; and wherein (i) at least a portion of the carbon dioxide is removed from the first effluent stream prior to feeding the first effluent stream to the second reactor in step (b); and/or (ii) at least a portion of the carbon dioxide is removed from the recycle stream prior to the step (d) of recycling a first portion of the recycle stream to the first reactor in step (a), and a second portion of the recycle stream to the second reactor in step (b).

16. An ethylene oxide (EO) production process comprising:
   (a) introducing a first reactant mixture to an oxidative dehydrogenation (ODH) reactor to produce a first effluent stream; wherein the first reactant mixture comprises ethane, and oxygen; and wherein the first effluent stream comprises ethylene, ethane, and oxygen;
   (b) introducing a second reactant mixture to an EO reactor to produce a second effluent stream; wherein the second reactant mixture comprises at least a portion of the first effluent stream; wherein ethylene is not separated from the first effluent stream; and wherein the second effluent stream comprises EO, ethane, ethylene, oxygen, and carbon dioxide;
   (c) separating at least a portion of the second effluent stream into an EO product stream and a recycle stream; wherein the EO product stream comprises at least a portion of the EO in the second effluent stream; wherein the recycle stream comprises ethane, ethylene, oxygen, and carbon dioxide; and wherein at least a portion of the carbon dioxide is optionally removed from the recycle stream;
   (d) recycling a first portion of the recycle stream to the ODH reactor in step (a), and a second portion of the recycle stream to the EO reactor in step (b); wherein ethylene is not separated from the recycle stream; wherein a recycle split ratio is defined as the ratio of the volumetric flowrate of the first portion of the recycle stream divided by the sum of the volumetric flowrate of the first portion of the recycle stream and the volumetric flowrate of the second portion of the recycle stream;
   (e) determining a molar concentration of ethylene in the recycle stream;

(f) comparing the molar concentration of ethylene in the recycle stream with a target molar concentration of ethylene in the recycle stream;

(g) responsive to step (f), when the molar concentration of ethylene in the recycle stream is less than the target molar concentration of ethylene in the recycle stream, increasing the recycle split ratio; and (h) responsive to step (f), when the molar concentration of ethylene in the recycle stream is greater than the target molar concentration of ethylene in the recycle stream, decreasing the recycle split ratio.

17. The process of claim 16, wherein the target molar concentration of ethylene in the recycle stream is from about 25 mol % to about 40 mol %.

18. The process of claim 16, wherein a concentration of ethane in the second reactant mixture and/or the recycle stream is from about 0.1 mol % to about 3 mol %.

19. The process of claim 16, wherein the ODH reactor is characterized by an ethane conversion of from about 70% to about 100%.

20. The process of claim 16, wherein the recycle split ratio is modified to be in a range of from about 0.2 to about 0.6.

* * * * *